United States Patent [19]

Chiang et al.

[11] 4,386,093

[45] May 31, 1983

[54] (±)3-DEAZAARISTEROMYCIN AND USES

[75] Inventors: Peter K. Chiang, Kensington; Giulio L. Cantoni, Bethesda, both of Md.; John A. Montgomery, Birmingham, Ala.

[73] Assignee: The United States of America as represented by the Secretary of the Department of Health and Human Services, Washington, D.C.

[21] Appl. No.: 302,557

[22] Filed: Sep. 16, 1981

[51] Int. Cl.$^3$ .................. A61K 31/435; C07D 471/04
[52] U.S. Cl. ..................................... 424/256; 546/118
[58] Field of Search ................. 424/180, 256; 546/118

[56] References Cited

U.S. PATENT DOCUMENTS

| | | | |
|---|---|---|---|
| 3,919,193 | 11/1975 | Mian et al. | 424/180 |
| 4,148,888 | 4/1979 | Cantoni et al. | 424/180 |
| 4,210,639 | 7/1980 | Chiang et al. | 424/180 |
| 4,309,419 | 1/1982 | Wolberg et al. | 424/180 |
| 4,315,000 | 2/1982 | Cook | 424/180 |

Primary Examiner—Ethel G. Love
Attorney, Agent, or Firm—John S. Roberts, Jr.

[57] ABSTRACT (±)3-Deazaaristeromycin, also known as (±)-4-amino-1-[(1α, 2β, 3β, 4α)-2,3-dihydroxy-4-(hydroxymethyl)-cyclopentyl]imidazo[4,5-c]pyridine, utilized as a novel antiviral agent and inhibiting S-adenosylhomocysteine hydrolase in a pharmacological target in effective concentrations.

8 Claims, No Drawings

(±)3-DEAZAARISTEROMYCIN AND USES

The invention described herein was made in the course of work under a grant or award from the Department of Health and Human Services.

This invention relates to the compound (±)3-deazaaristeromycin, also known as (±)-4-amino-1-[(1α, 2β, 3β, 4α)-2,3-dihydroxy-4-(hydroxymethyl)-cyclopentyl]imidazo[4,5-c]pyridine, utilized as a novel antiviral agent and inhibiting S-adenosylhomocysteine hydrolase in a pharmacological target in effective conentrations.

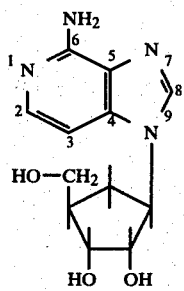

Prior Art Statement

U.S. Pat. No. 3,919,193 Mian et al—3-deazaguanosine and related compounds useful as antiviral agents.

U.S. Pat. No. 4,148,888 Cantoni et al—3-deazaadenosine as an inhibitor of adenosylhomocysteine hydrolase with antiviral activity.

U.S. Pat. No. 4,210,639 Chiang et al—5'-deoxy-5'-(isobutylthio)-3-deazaadenosine, method of making same and its antiviral effect on rouse sarcoma virus and gross murine leukemia virus.

Theory of Operation in the Cell

A novel analog of adenosine, (±)3-deazaaristeromycin, has been synthesized. (±)3-Deazaaristeromycin is a very potent antiviral agent in cell cultures against herpes simplex type I and HL-23 C type virus. It is relatively non-cytotoxic at the effective antiviral concentrations used and is not subject to deamination or phosphorylation. With a $K_I$ of $3 \times 10^{-6}$ M, it acts as a competitive inhibitor of S-adenosylhomocysteine hydrolase without being a substrate. (±)3-Deazaaristeromycin causes a selective inhibition of the methylation of the polynucleotide 5' cap of viral mRNA via higher cellular concentrations of S-adenosylhomocysteine as a result of the inhibition of S-adenosylhomocysteine hydrolase. Increases in the intracellular level of S-adenosylhomocysteine hydrolase in cells were observed after incubation with (±)3-deazaaristeromycin.

S-Adenosylmethionine (AdoMet) dependent methylation reactions exhibit a wide range of sensitivity toward inhibition by S-adenosylhomocysteine (AdoHcy), one of the products of methylation reactions. Because of this variable sensitivity, analogs of adenosine or AdoHcy have been synthesized and tested for their ability to inhibit AdoHcy hydrolase, which hydrolizes AdoHcy to homocysteine and adenosine. Although the equilibrium of the reaction favors synthesis, physilogically the reaction proceeds in the hydrolytic direction because adenosine and homocysteine are removed by metabolism. When AdoHcy hydrolase is inhibited, cellular accumulation of AdoHcy takes place.

The pharmacological consequence is a disruption of the cellular ratio of AdoMet/AdoHcy, leading to a selective perturbation of methylation reactions. Until now, one of the more potent inhibitor found for AdoHcy hydrolase is 3-deazaadenosine. However, depending on species and organs, 3-deazaadenosine can also serve a substrate for AdoHcy hydrolase generating 3-deaza-AdoHcy. It is normally difficult to discriminate whether AdoHcy or 3-deaza-AdoHcy is the pharmacological agent responsible for the biochemical and biological effects observed. These effects are: inhibition of phospholipid methylation and creatine biosynthesis in vivo; inhibition of protein carboxymethylation; inhibition of chemotaxis and phagocytosis; inhibition of histamine release by human basophils; inhibition of lymphocyte-mediated cytolysis; anti-marlarial effect in vitro; conversion of 3T3-L1 fibroblasts to fat cells; and antiviral effects.

The concept of exploiting AdoHcy hydrolase as a pharmacological target for chemotherapeutic purposes has been proposed previously by Chiang et al, Mol. Pharmacol. 13, 939–947 (1977) and Chiang et al, Biochem. Pharmacol. 28, 1897–1902 (1979). Particularly notable is the observation that 3-deazaadenosine is a potent antiviral agent against a variety of DNA and RNA viruses. The RNA viruses that are affected are Rous sarcoma virus, vesicular stomatitis, Sindbis, Newcastle disease, and HL-23. The DNA viruses that are affected are simian virus 40 and herpes simplex type I.

The finding that (±)aristeromycin is the most potent inhibitor for AdoHcy hydrolase, with a $K_i$ of $10^{-9}$ M, led to the synthesis of (±)3-deazaaristeromycin (3-deaza-Ari). 3-Deaza-Ari is a competitive inhibitor of AdoHcy hydrolase with a $K_i$ of 3 uM and is not a substrate for AdoHcy hydrolase. It exhibits negligible or very little irreversible inhibition of the enzyme in vitro. It is not deaminated by calf intestinal deaminase and is not phosphorylated by adenosine kinase, in contrast to (±)aristeromycin.

In terms of antiviral potency, 3-deaza-Ari is 10–100 times better than 3-deazaadenosine. Table 1 shows that at 20 μM, 3-deaza-Ari inhibited the plaque formation of herpes I by 97%, and at 30 μM, herpes I was inhibited by more than 99%. Very little cytotoxicity was observed for the mouse L cells; at most there was a 5% reduction in the cell number. Vaccinia virus was also very sensitive to inhibition by 3-deaza-Ari. The plaque formation by vaccinia virus was inhibited by more than 99% at 1 μM without any cytotoxicity.

The virus production by HL-23, a C type virus isolated from human acute myelogenous leukemia cells, was inhibited by more than 85% at 0.5 uM 3-deaza-Ari (Table 1). Moreover, the induction of oncogenic transformation of normal rat kidney cells (NRK 153 Cl 7) by HL-23 virus was also inhibited. At 1 μM, 3-deaza-Ari inhibited the foci formation of HL-23 by 76% and at 2 μM by about 96%. The selectivity ratio, i.e., the highest noncytotoxic concentration of drug over the lowest effective concentration of drug, was >8.

The antiviral effect of 3-deaza-Ari could be correlated with the accumulation of AdoHcy in the cells due to the inhibition of AdoHcy hydrolase by 3-deaza-Ari. The AdoHcy hydrolase of NRK 153 Cl 7 cells was more sensitive to inhibition by 3-deaza-Ari. Two hours after the administration of 1 μM 3-deaza-Ari, there was a 5-fold increase in AdoHcy, which rose further to 30-fold after 24 hours. Accompanying the increase of AdoHcy was a steady increase of 1.3-fold of AdoMet in these cells. The response of the mouse L cells to 3-deaza-Ari was somewhat different. Paralleling the 2- to 3-fold increase in AdoHcy was a 2-fold increase in AdoMet. Twenty-four hours after the administration of 30 μM 3-deaza-ARi, the level of AdoMet returned to normal when the rise of AdoHcy subsidized. The overall increase in the cellular levels of AdoMet in these 2 types of cells was probably a reflection of inhibition of methylation reactions.

The most likely mechanism for the antiviral activity of 3-deaza-Ari is the inhibition of the methylation of the 5' cap of mRNA of the viruses by the higher than normal accumulation of cellular AdoHcy. The methylation of the 5' polynucleotide cap of mRNA is essential for viral replication. One evidence to support this is that both 3-deaza-ARi and 3-deazaadenosine fail to inhibit the replication of poliovirus, which has a polypeptide cap the 5' end and is not methylated. 3-Deaza-Ari compares favorably well in potency with another commercial antiviral agent, acycloguanosine. However, unlike acycloguanosine, 3-deaza-Ari cannot be phosphorylated and is not incorporated into nucleotides that can become part of the genome of the host. Furthermore, 3-deaza-Ari does not inhibit chemotaxis by neutrophilis or macrophage cell lines, in contrast to 3-deazaadenosine.

For tissue culture use against antiviral activity of 3-deazaaristeromycin against herpes simplex can be in a dosage of 10–70 μM; against HL-23, 0.25 to 1.00 μM; against HL-23 foci formation, 0.25 to 4.00 μM; and against vaccinia, 0.5 to 4.00 μM.

TABLE 1

Antiviral activity of (±)3-deazaaristeromycin on herpes simplex type I, HL-23 C type virus, and vaccinia virus.

| Virus | 3-Deazaaristeromycin(uM) | % Inhibition | % Control Cell Number |
|---|---|---|---|
| Herpes I | 10 | 60 | 100 |
| (Plaque formation) | 20 | 97 | 95 |
| | 30 | 9917 | 95 |
| | 40 | 99.3 | 91 |
| | 50 | 99.3 | 95 |
| | 60 | 100 | 91 |
| | 70 | 100 | 82 |
| HL-23 | 0.25 | 68 | 100 |
| (Virus production) | 0.50 | 86 | 88 |
| | 1.00 | 86 | 75 |
| HL-23 | 0.25 | 44 | 100 |
| (Foci formation) | 0.50 | 44 | 96 |
| | 1.00 | 76 | 81 |
| | 2.00 | 92 | 71 |

TABLE 1-continued

Antiviral activity of (±)3-deazaaristeromycin on herpes simplex type I, HL-23 C type virus, and vaccinia virus.

| Virus | 3-Deazaaristeromycin(uM) | % Inhibition | % Control Cell Number |
|---|---|---|---|
| | 4.00 | 99 | 53 |
| Vaccinia | 0.5 | 84 | 120 |
| (Plaque formation) | 1.0 | 99.2 | 144 |
| | 2.0 | 99.6 | 111 |
| | 4.0 | 99.8 | 111 |

Herpes type I was grown in mouse L cells and the plaques were determined on day 3; virus production by HL-23 was measured with NRKB/HL-23 cells on day 3; oncogenic transformation by HL-23 was assayed by infecting normal rat kidney cells (NRK 153 Cl 7) with HL-23 and the foci counted on day 5 after staining with Giemsa.

We claim:
1. A method of alleviating the effects of herpes simplex type I by utilization of an effective concentration for the inhibition of herpes simplex I in tissue culture of (±)-3-deazaaristeromycin.
2. A method of alleviating the effects of HL-23 C type virus by utilization of an effective concentration for the inhibition of HL-23 type virus in tissue culture of (±)-3-deazaaristeromycin.
3. A method of alleviating the effects of vaccinia virus by utilization of an effective concentration for the inhibition of vacinnia virus in tissue culture of (±)-3-deazaaristeromycin.
4. The compound (±)-3-deazaaristeromycin:

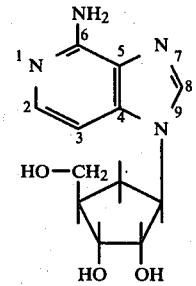

5. A composition for alleviating the effects of a virus substrate selected from the group consisting of herpes simplex type I, HL-23 type and vaccinia virus which comprises utilizing an effective concentration for the inhibition of a virus substrate selected from the group consisting of herpes simplex type 1, HL-23 type virus and vaccinia virus in tissue culture of (±)-3-deazaaristeromycin.
6. The composition according to claim 5 wherein the virus is herpes simplex type I.
7. The composition according to claim 5 wherein the virus is HL-23 type.
8. The composition according to claim 5 wherein the virus is vaccinia virus.

* * * * *